United States Patent [19]

Mansson

[11] 4,170,755

[45] Oct. 9, 1979

[54] FM TRANSMITTER AND RECEIVER FOR USE WITH NON-DESTRUCTIVE TESTING APPARATUS INCLUDING A MOVEABLE HEAD

[75] Inventor: Sven E. Mansson, Hollviksnas, Sweden

[73] Assignee: Magnetic Analysis Corporation, Mount Vernon, N.Y.

[21] Appl. No.: 827,228

[22] Filed: Aug. 24, 1977

[51] Int. Cl.$^2$ ............................................. G01R 33/12
[52] U.S. Cl. ................................... 324/238; 324/240; 324/242
[58] Field of Search ............... 324/208, 237, 238, 240, 324/241, 242; 329/126, 128; 307/233 R, 261, 237, 295; 328/21, 28, 140

[56] References Cited

U.S. PATENT DOCUMENTS

| | | | |
|---|---|---|---|
| 2,340,609 | 2/1944 | Mestas | 324/208 |
| 2,530,081 | 11/1950 | Ross | 329/126 |
| 2,956,227 | 10/1960 | Pierson | 329/128 |
| 3,170,113 | 2/1965 | Harmon | 324/237 |

Primary Examiner—Robert J. Corcoran
Attorney, Agent, or Firm—Pennie & Edmonds

[57] ABSTRACT

Transducer means mounted on a moving head produce test signals which modulate an FM transmitter on the moving head. A stationary FM receiver has demodulation means including a toggle flip-flop supplied with an FM signal corresponding to the transmitted signal, preferably an IF signal. The flip-flop changes state when its input passes through a threshold level and yields a rectangular wave output, and preferably also the inversion thereof. Short pulses are produced at edges of the rectangular wave, as by differentiation. The short pulses are applied to a sawtooth generator, preferably of the constant charging current type, to produce sawtooth waves whose amplitude and duration are proportional to the periodicity of the pulses. The sawtooth waves are filtered and the output applied to apparatus for processing and indicating variations in the object being tested. The output varies as an inverse function of frequency of the signal applied to the flip-flop and is corrected by non-linear amplifying means, advantageously connected in the modulating path of the FM transmitter.

3 Claims, 5 Drawing Figures

FM TRANSMITTER AND RECEIVER FOR USE WITH NON-DESTRUCTIVE TESTING APPARATUS INCLUDING A MOVEABLE HEAD

This invention relates to apparatus for the non-destructive testing of objects in which test signals produced on a moving head are supplied to stationary apparatus for processing the test signals and indicating variations in an object under test.

In non-destructive testing apparatus, for example of the eddy current, leakage flux and ultrasonic pulse types, etc., frequently transducer means are mounted on a moving head, usually a rotating head, and produce signals corresponding to variations in an object under test. These signals are fed to stationary apparatus including amplifiers, detectors, filters, etc. for processing the signals and indicating variations in the object due to flaws, defects, etc. In some types of apparatus energizing signals are also fed from the stationary apparatus to the rotating head. Commonly slip rings, rotary transformers, rotary capacitors, etc. are employed to feed the signals from the rotating head to the stationary equipment, and vice versa.

In feeding the test signals to the stationary equipment it is important to minimize noise as much as possible, and frequently a wide transmission band is required. Slip rings, rotary transformers and rotary capacitors become quite expensive in order to meet these requirements, and even then may not be fully satisfactory.

The present invention employs frequency modulated (FM) transmission to transmit signals from the moving head to the stationary equipment, and vice versa if desired.

Conventional FM receiver demodulators require very effective limiting to eliminate the effect of amplitude modulation (AM) on the received signals and yield a noise-free signal. Also the frequency deviation is usually a very small percentage of the carrier frequency when a linear output is desired. The present invention provides a demodulation arrangement which does not require a limiter and will accept a very large frequency deviation or percentage of modulation, while at the same time being quite economical.

In accordance with the present invention, non-destructive testing apparatus is provided which comprises a moving head, advantageously a rotating head, on which transducer means are mounted for producing test signals corresponding to variations in an object under test. An FM transmitter is mounted on the moving head and transmits a frequency modulated signal modulated in accordance with the test signals. An FM receiver stationary with respect to the moving head receives the transmitted signal. Demodulation means in the receiver includes a toggle flip-flop supplied with a frequency modulated signal corresponding to the received signal, preferably an intermediate frequency (IF) signal. The flip-flop is designed and adapted to change state when the input thereto passes a threshold level in a predetermined polarity direction and yields a corresponding rectangular wave output. Short pulses are produced at predetermined edges of the flip-flop output and supplied to a sawtooth generator which produces sawtooth waves having amplitudes proportional to the periodicity of the pulses. Means responsive to the sawtooth waves indicates variations in the object under test.

The demodulation is substantially noise-free and unaffected by AM modulation of the FM signal, and limiting circuits are unnecessary.

Advantageously, two rectangular wave outputs of the flip-flop, inverted with respect to each other, are applied to respective differentiating circuits to produce short pulses at successive edges of the waves, and the sawtooth generator produces sawtooth waves of predetermined slope with both the amplitude and duration thereof proportional to the periodicity of the pulses. The sawtooth waves are then supplied to a filter which produces an output corresponding to the test signals, and the output is processed and indicated as desired.

With both amplitude and duration of the sawtooth waves proportional to the periodicity of the pulses, the output varies as an inverse function of the frequency of the signals applied to the flip-flop. This is corrected by non-linear amplifying means, preferably connected in the modulating path of the FM transmitter.

DETAILED DESCRIPTION OF THE DRAWINGS

Figure 1:
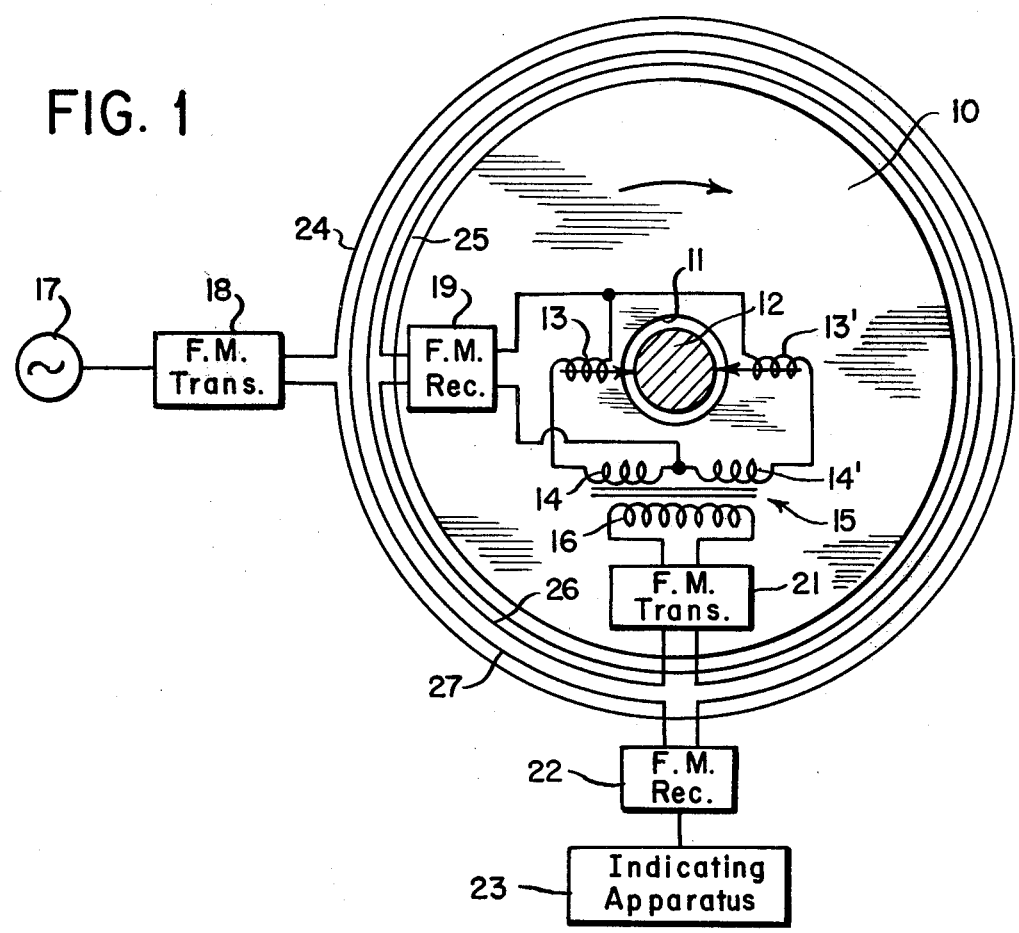
FIG. 1 is a schematic illustrating eddy current test apparatus employing the invention.

Referring to FIG. 1, a rotating head 10 has a central opening 11 through which object 12 is fed during testing. A pair of probes 13, 13' are mounted on the rotating head and each may be a coil with a ferrite core, or other suitable design. The probes are connected in a bridge circuit including center-tapped windings 14, 14' of a transformer 15 having an output winding 16.

The probes are energized from a source 17 of alternating current or by DC pulses, as desired. The source is connected to a stationary FM transmitter 18 whose signals are received and demodulated by an FM receiver 19 mounted on rotating head 10, and the demodulated signal is applied across one diagonal of the bridge. The signal from source 17 may be considered as a carrier and, in the absence of flaws, defects or other variations in object 12, the signal is nulled by the balanced bridge configuration. In the presence of flaws, defects, etc. in the object, the carrier is modulated in amplitude and/or phase. This produces an unbalanced signal in the bridge and yeilds test signals in winding 16 of the transformer varying from the null condition. The test signals modulate the FM transmitter 21 which is mounted on the rotating head 10. The transmitted signals are received and demodulated by a stationary FM receiver 22 and the resultant test signal output supplied to indicating apparatus 23.

The indicating apparatus 23 may be designed as known in the field of eddy current testing to process the test signals and yield a desired indication of flaws, defects, etc. in the object under test. For example, the signals may be quadrature detected, amplified and filtered, and displayed on a cathode-ray oscilloscope (CRT), as shown for example in my U.S. Pat. No. 3,900,793.

The FM signals may be transmitted and received by very simple antennas. In FIG. 1 simple loops are employed. Thus stationary loop 24 serves to transmit the signal from 18 to a loop 25 mounted on the rotating head 10 and connected to receiver 19. A rotating loop 26 mounted on the head 10 transmits the signal from the transmitter 21 to a stationary loop 27 connected to receiver 22. Mounting details are omitted, since the loops may be insulated wires mounted on the surfaces of the rotating head and on a stationary structure. Other forms of antennas may be employed if desired.

Figure 2:
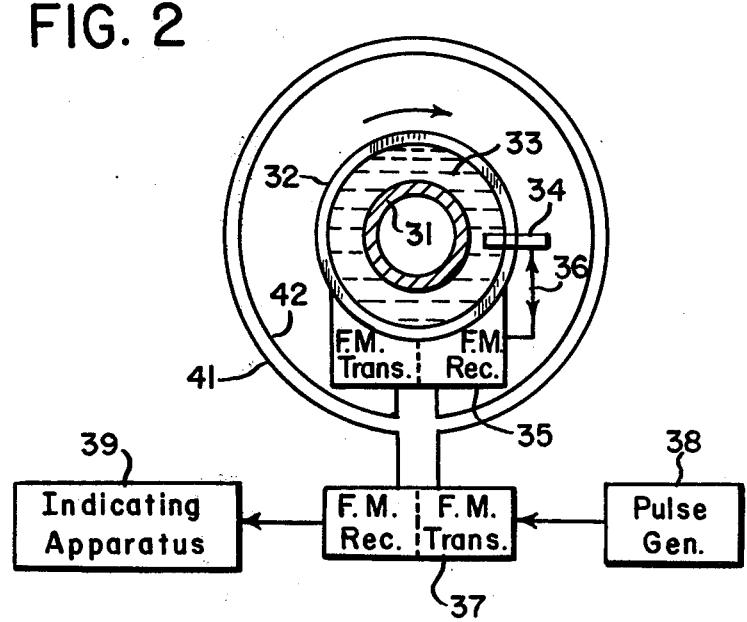
FIG. 2 illustrates ultrasonic test apparatus employing the invention.

FIG. 2 illustrates ultrasonic non-destructive testing apparatus. Here an object 31 to be tested is inserted in a rotating cylinder 32, the space 33 between the object and the cylinder being filled with a suitable couplant liquid such as water. One or more ultrasonic transducers such as indicated at 34 are mounted on the rotating cylinder 32. FM transmitter and receiver circuits are mounted on the rotating cylinder 32 as indicated at 35 and connected by line 36 to transducer 34 so as to supply energizing pulses to the transducer and receive test signals from the transducer corresponding to echoes reflected from discontinuities in the object.

Stationary FM transmitter and receiver circuits are indicated at 37. Pulses from generator 38 are supplied to the FM transmitter portion of 37, and are received by the FM receiver portion of 35 and supplied to transducer 34. Test signals from the transducer are supplied to the transmitter portion of 35, and are received by the receiver portion of 37 and supplied to indicating apparatus 39. Simple loop antennas are employed, loop 41 being stationary and loop 42 being mounted on rotating cylinder 32.

In the case of leakage flux testing apparatus, it is commonly unnecessary to supply signals to the rotating head. Thus one or more FM transmitters may be mounted on the rotating head, and one or more stationary FM receivers employed.

Figure 3:
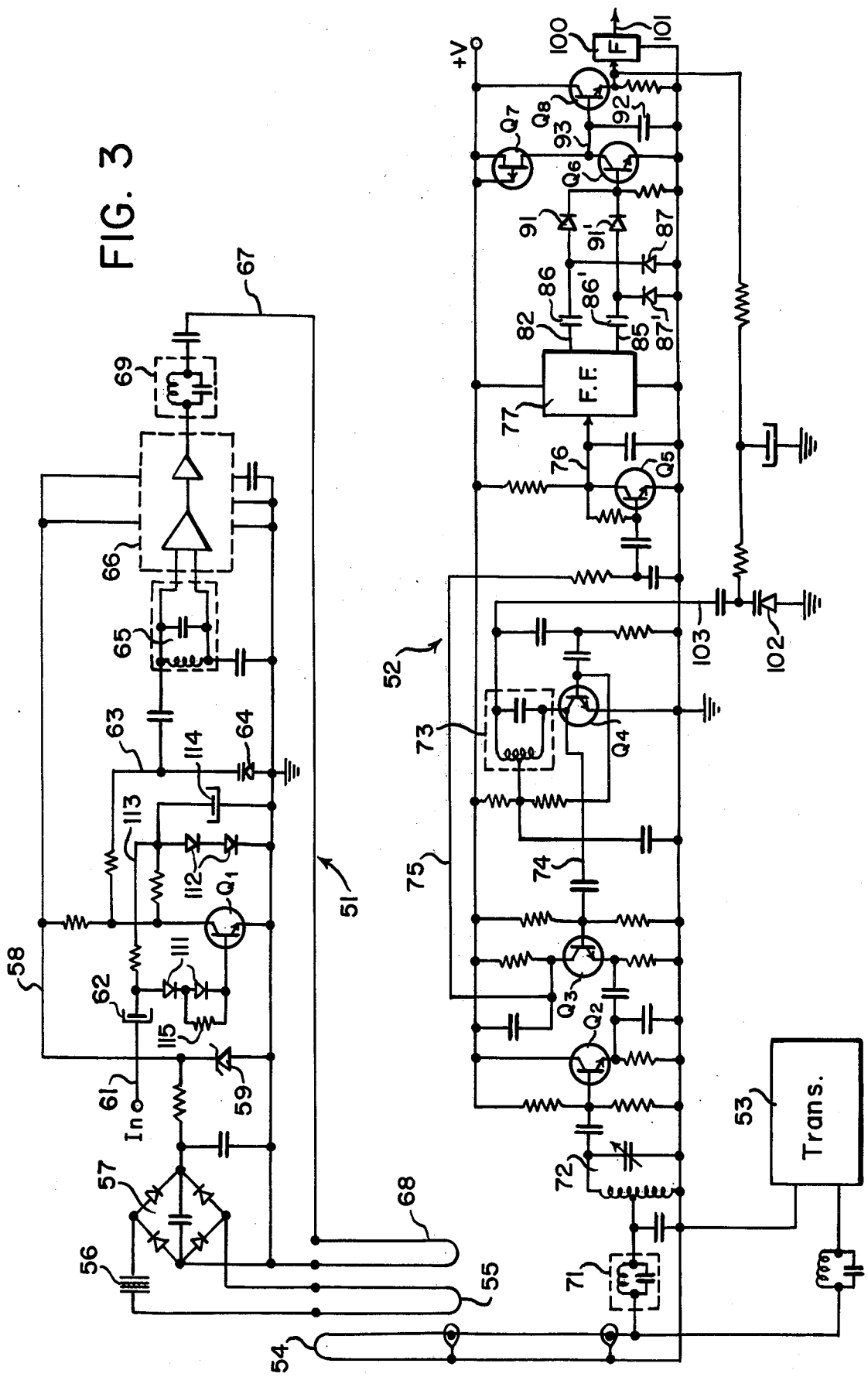
FIG. 3 is a circuit diagram of an FM transmitter and receiver in accordance with the invention.

Referring to FIG. 3, the upper part of the figure denoted by the arrow 51 shows the FM transmitter circuits and the lower part denoted by the arrow 52 shows the FM receiver circuits. It is assumed that the transmitter circuits are mounted on a moving head such as the rotating platform 10 of FIG. 1 or the rotating cylinder 32 of FIG. 2.

With a transistorized transmitter as shown, the current requirements are quite small and batteries could be mounted on the rotating head if desired. Here, however, the power is transmitted. Transmitter 53 is a continuous wave transmitter whose frequency is outside those used for FM transmission, say 27 MHz (megahertz). Antenna 54 transmits the continuous wave to antenna 55. A crystal 56 tuned to the frequency of transmitter 53 supplies the received wave to a full wave rectifier 57 whose output is filtered to supply a DC voltage to line 58. Zener 59 maintains the voltage constant.

Input line 61 is supplied with test signals from the transducer and associated circuit means of the non-destructive test apparatus, for example, the signals from the transformer output winding 16 of FIG. 1 or line 36 of FIG. 2. The signals in line 61 are coupled by a large capacitor 62 to a non-linear amplifier including transistor Q1 whose functioning will be described later. The output of the amplifier in line 63 is applied to a variable capacitance diode 64 whose capacitance varies with the signal in line 63. Diode 64 shunts the tank circuit 65 of the transmitter RF generator indicated by the dotted box 66. Accordingly the diode 64 serves as the frequency modulating element of the FM transmitter. The FM transmitter may be of known type and further description is believed unnecessary.

The FM modulated signal is supplied through line 67 to a transmitting antenna 68 mounted on the rotating head. A wave trap 69 tuned to the transmitter power supply frequency (e.g. 27 MHz) blocks that frequency.

Considering now the receiver circuits, antenna 54 also functions as a receiving antenna and is connected through a wave trap 71 (tuned to the frequency of 53) to a receiver tank circuit 72 tuned to the FM transmitter frequency. The FM signal is applied to transistor Q2 functioning as an emitter follower, and then to a mixer stage including transistor Q3. RF amplification may be employed if desired. Transistor Q4 with tank circuit 73 serves as the local oscillator of a super-heterodyne circuit. The local oscillator frequency is supplied through line 74 to mixer Q3, and the resultant intermediate frequency (IF) is produced in line 75.

The transmitter frequency and the local oscillator frequency, and the resultant intermediate frequency, may be chosen as desired for the particular application. Certain aspects will be discussed later.

The IF signal in line 75 is amplified by Q5 and supplied through line 76 to a toggle flip-flop 77. As will be understood, the frequency modulated signal in line 75 corresponds to the received frequency modulated signal, since all the frequencies in the received signal have been changed by like amounts. The toggle flip-flop is of the type which changes state when the input thereto passes a threshold level in a predetermined polarity direction and yields a corresponding rectangular wave output. Such flip-flops are known in the art, and an example is the so-called JK flip-flop which is commercially available as an integrated circuit. The functioning is illustrated in FIG. 4.

Figure 4:
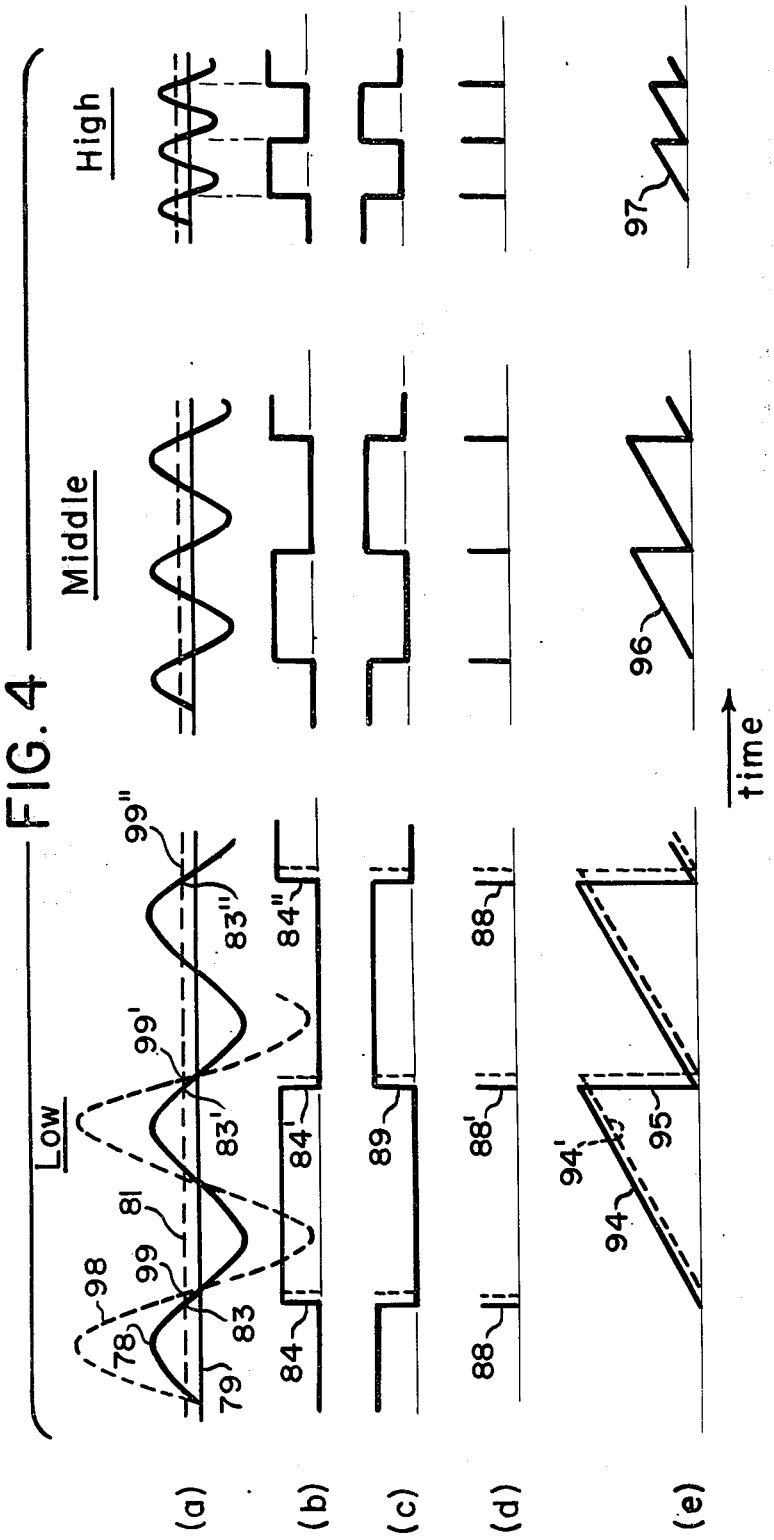
FIGS. 4-5 are waveforms explanatory of the circuit of FIG. 3.

FIG. 4 has three columns illustrating the response to low, middle and high frequency signals in line 76. In the first column, at (a), a low frequency signal 78 is shown which varies about a reference potential 79. Dash line 81 is the threshold level of the flip-flop. Whenever the signal 78 passes the threshold level 81 in the negative going direction, the flip-flop changes state. One output of the flip-flop is shown at (b), corresponding to output line 82. At point 83, the output in line 82 goes from low to high level forming edge 84 of a rectangular wave output. At point 83', the output in line 82 goes low at edge 84', and at 83" it goes high at edge 84". The output of the flip-flop in line 85 is the inverse of that in line 82, as shown at (c).

The outputs in lines 82 and 85 are supplied to respective differentiating circuits fromed by series capacitors 86, 86' and shunt diodes 87, 87' to produce short pulses at successive edges of the rectangular waves as shown at (d). Diodes 87, 87' effectively short circuit the negative differentiated pulses to ground. Thus positive pulses 88 are produced at positive-going edges 84 and 84" of (b) and positive pulse 88' at edge 89 of (c). The short positive pulses are fed to the base of transistor Q6 through series diodes 91, 91'.

Capacitor 92 is charged through a constant current source formed by FET Q7, and is discharged by Q6 each time a pulse is applied to its base. Thus sawtooth waves are produced in line 93 which have a constant slope as shown at 94 of (e). The duration of the sawtooth wave is equal to the period of the wave 78 in (a), and the amplitude 95 is proportional to the period of wave 78.

The Middle and High frequency columns of FIG. 4 show similar graphs for higher frequency input waves to flip-flop 77, yielding sawtooth waves 96 and 97. As will be noted, the durations of the sawtooth waves are proportional to the periodicity of the pulses in (d) and hence to the periodicity of the signals in (a). Also, inasmuch as the slopes of the sawtooth waves in (e) are the same for all frequencies, the amplitudes are proportional to the periodicity of the pulses. Thus a frequency modulated input to flip-flop 77 will produce a sawtooth wave output in line 93 which changes in amplitude as the input frequency varies. By choice of power supply voltage +V, capacitor 92 and the constant current source Q7, large amplitude outputs can readily be obtained.

Considering now the immunity of the circuit to amplitude modulation, FIG. 4(a) shows a dotted input wave 98 whose amplitude is much greater than 78. The points 99, 99' and 99" at which wave 98 passes the threshold level 81 are slightly displaced from points 83, 83' and 83", resulting in a slight displacement of the rectangular waves in (b) and (c) as shown dotted, and hence a slight displacement of the pulses in (d) as shown dotted. Thus the dotted sawtooth wave 94' in (e) will be slightly displaced. However, the charging time of capacitor 92 will be unchanged, since the period of the pulses in (d) is unchanged. Hence there will be little if any effect on the demodulated output.

Although sine waves are shown in FIG. 4 for convenience of explanation, it will be understood that in practice distortion may be present. With flip-flop 77 of the type described above, which changes state when the applied wave passes the threshold in one polarity direction only, considerable distortion may be present without adversely affecting the operation.

The sawtooth output in line 93 is applied to an emitter follower Q8 and then to a filter 100. The filter may be a simple R-C low pass filter giving an output proportional to the peaks of the sawtooth waves, or other suitable design. Thus the output of the filter in line 101 corresponds to the input signal to the transmitter, and may be processed and indicated as desired.

Automatic frequency control (AFC) may be employed if desired. To this end the output of Q8 is fed back through a resistor-capacitor circuit to a variable capacitance diode 102 which is connected through a capacitor and line 103 to the tank circuit 73 of the local oscillator. The AFC circuit may follow conventional design and need not be described further.

With sawtooth waves whose duration and amplitude are both proportional to the periodicity of the pulses of FIG. 4(d), and hence to the periodicity of the applied waves of (a), it is found that the output varies as an inverse function of the frequency of the IF signal applied to flip-flop 77.

Figure 5:
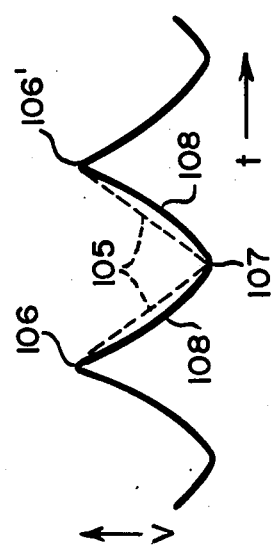

This is illustrated in FIG. 5. If a triangular voltage wave such as illustrated by the dotted lines 105 were applied to the modulating circuit of the FM transmitter, as at line 63 of FIG. 3, the RF transmitted signal would have a similar frequency variation. With the frequency of the local oscillator Q4 above the transmitter frequency, the IF signal in line 76 would be the inversion of 105. Thus points 106, 106', would correspond to low frequencies of the IF signal and point 107 to a high frequency of the IF signal. Inasmuch as the amplitudes of the output sawtooth waves are proportional to the period of the IF signal, which is the inverse of frequency, points 106, 106' correspond to longer periods and point 107 to a shorter period of the IF signal. The resulting output in line 101 is shown by the full lines 108. As will be observed, lines 108 are not linear.

The non-linearity may be corrected by a non-linear amplification of the output from line 101. It is preferred, however, to perform the non-linear amplification in the modulating path of the transmitter. This is accomplished by Q1 and its associated circuits in the transmitter of FIG. 3, which form an amplifier of the exponential or logarithmic type.

Diodes 111 are connected in the input circuit of Q1 and diodes 112 are connected in the output circuit with feedback through line 113 to the input circuit. Diodes 112 are shunted by a large capacitor 114. At low operating levels the diodes have non-linear characteristics and consequently the output signal in line 63 is non-linear with respect to the input signal in line 61. The amount of non-linearity may be determined by suitably selecting the operating parameters and by shunting one of diodes 111 by resistor 115. The general principles of non-linear amplification are known, and further detailed description of the circuit shown is believed unnecessary.

With the non-linear amplification produced by Q1 and the associated diodes and circuit elements, the distortion illustrated at 108 in FIG. 5 may be corrected, and a linear output as illustrated at 105 may be obtained.

If desired, the local oscillator frequency may be below the transmitter frequency, with suitable change in the non-linear correction if required.

With the arrangement shown, it has been found that wide frequency deviations are possible while maintaining adequate output linearity. For example, transmitter frequencies of 10 MHz and 30 MHz have been employed with success, with local oscillator frequencies yielding intermediate center frequencies of 500 KHz. Frequency deviations approaching ±500 KHz have been employed, and outputs of the order of 3.5 volts with a 5.0 volt power supply have been obtained. Larger outputs can readily be obtained with a higher voltage supply to the sawtooth generating circuit, without additional amplification. Other transmitter and intermediate frequencies can be employed if desired. With small frequency deviations it may be unnecessary to employ non-linear correction, but the arrangement described will still have the other advantages described hereinbefore.

It will be understood that although the description of FIG. 5 is for a triangular wave input, for convenience of explanation, the actual inputs from the transducers to the transmitter will vary widely.

If desired the D-C power to the rotating head may be supplied by slip rings and brushes, or A-C may be supplied by a rotary transformer with rectification and filtering on the rotating head, and transmitter 53 and associated traps 71 and 69 omitted.

The term "antenna" has been used hereinbefore in its broad sense. It will be understood that with the simple loops shown in the specific embodiments, the transmitter signal is fed to the receiver primarily by inductive coupling.

I claim:

1. In an apparatus for the non-destructive testing of objects, said apparatus having a moving head moving relative to the object and transducer means mounted thereon for producing test signals corresponding to variations in an object under test, the improvement comprising;

a. an FM transmitter mounted on said moving head for transmitting a frequency modulated signal modulated in accordance with said test signals, b. an FM receiver stationary with respect to said moving head for receiving said frequency modulated signals, c. demodulation means in said FM receiver including a toggle flip-flop supplied with a frequency modulated signal corresponding to the received frequency modulated signal, d. said flip-flop being designed and adapted to change state when the input thereto passes a threshold level in a predetermined polarity direction and yield a corresponding rectangular wave output, e. means responsive to said rectangular wave for producing short pulses at predetermined edges thereof;

f. a sawtooth wave generator means supplied with said short pulses for producing sawtooth waves of predetermined slope having amplitudes and durations proportional to the periodicity of the pulses, g. and means responsive to said sawtooth waves for producing an output indicating variations in the object under test.

2. An apparatus according to claim 1 further comprising non-linear amplifier means connected in the modulating path of said FM transmitter for rendering said output substantially linear with test signals.

3. In an apparatus for the non-destructive testing of objects, said apparatus having a moving head moving relative to the object and transducer means mounted thereon for producing test signals corresponding to variations in an object under test, the improvement comprising;

a. an FM transmitter mounted on said moving head for transmitting a frequency modulated signal modulated in accordance with said test signals, b. non-linear amplifying means mounted on said moving head and connected between said transducer means and the modulating circuit of said transmitter for non-linearity amplifying said test signals and correspondingly modulating the transmitted signal, c. an FM receiver stationary with respect to said moving head for receiving said frequency modulated signal, d. local oscillator and mixer means in said receiver for converting the received signal to a correspondingly modulated intermediate frequency signal, e. demodulation means in said receiver including a toggle flip-flop supplied with said intermediate frequency signal, f. said flip-flop being designed and adapted to change state when the input thereto passes a threshold level in a predetermined polarity direction and yield a corresponding rectangular wave output and the inversion thereof, g. differentiating means for differentiating the rectangular wave outputs of said flip-flop to produce short pulses at successive edges thereof, h. a sawtooth wave generator including a capacitor, a constant current charging circuit for the capacitor and a discharge circuit, i. means supplying said short pulses to said discharge circuit for producing sawtooth waves of constant slope with amplitudes and durations proportional to the periodicity of the pulses, j. the magnitude of said sawtooth waves being dependent upon the voltage supplied to said sawtooth wave generator, k. filter means supplied with said sawtooth waves for producing an output corresponding to said test signals, l. said output varying as an inverse function of the frequency signal and said non-linear amplifying means being designed and adapted to correct for said inverse function and render the output substantially a linear function of said test signals.

* * * * *